US006409762B1

United States Patent
Pynson et al.

(10) Patent No.: US 6,409,762 B1
(45) Date of Patent: Jun. 25, 2002

(54) FLEXIBLE MONOBLOC INTRAOCULAR LENS

(75) Inventors: Joël Pynson, Toulouse; Florian David, Balma, both of (FR)

(73) Assignee: Chauvin Opsia, Z.A.C., Castanet Tolosan (FR)

( * ) Notice: Subject to any disclaimer, the term of this patent is extended or adjusted under 35 U.S.C. 154(b) by 0 days.

(21) Appl. No.: 09/646,463

(22) PCT Filed: Mar. 16, 1999

(86) PCT No.: PCT/EP99/00589

§ 371 (c)(1),
(2), (4) Date: Sep. 19, 2000

(87) PCT Pub. No.: WO99/48442

PCT Pub. Date: Sep. 30, 1999

(30) Foreign Application Priority Data

Mar. 20, 1998 (FR) .............................................. 98.03461

(51) Int. Cl.[7] .................................................. A61F 2/16
(52) U.S. Cl. ..................................... 623/6.39; 623/6.47
(58) Field of Search ............................. 623/6.11, 6.14, 623/6.18, 6.37–6.55, 6.13, 6.72, 6.24, 6.27–6.39, FOR 105

(56) References Cited

U.S. PATENT DOCUMENTS 4,629,462 A * 12/1986 Feaster ...................... 623/6.51

FOREIGN PATENT DOCUMENTS

| DE | 297 10 967 | 8/1997 | |
|---|---|---|---|
| EP | 0 579 528 | 1/1994 | |
| EP | 0 592 813 | 4/1994 | |
| EP | 0 766 952 | 4/1997 | |
| RU | 1811395 A3 * | 4/1993 | ........ 623/FOR 105 |
| WO | WO 97/41805 | 11/1997 | |

* cited by examiner

Primary Examiner—David H. Willse
(74) Attorney, Agent, or Firm—Young & Thompson

(57) ABSTRACT

The invention concerns a monobloc intraocular lens made of a flexible material comprising a central optic part (1) and a haptic part (4) including two loops (5) in contact with an internal wall of the eye and, for each contact loop (5), two elements (10, 10') to be linked with the optic part (1), the lens having a symmetry with respect to two perpendicular axes (6, 8), the external surface (9) of each contact loop (5) having a convex-shaped curve defining an apex (S), and two end points (E, E'). The circle (Ca) passing through the apex (S) and the two end points (E, E') has a diameter $\phi a$ greater than or equal to the mean diameter $\phi m$ of the ocular housing, and less than $\phi m+1.5$ mm. The apices (S) are separated from each other by a distance $D>\phi a$ and the linking elements (10, 10') are adapted so as to be deformable in flexion in the principal plane (3) of the lens.

35 Claims, 5 Drawing Sheets

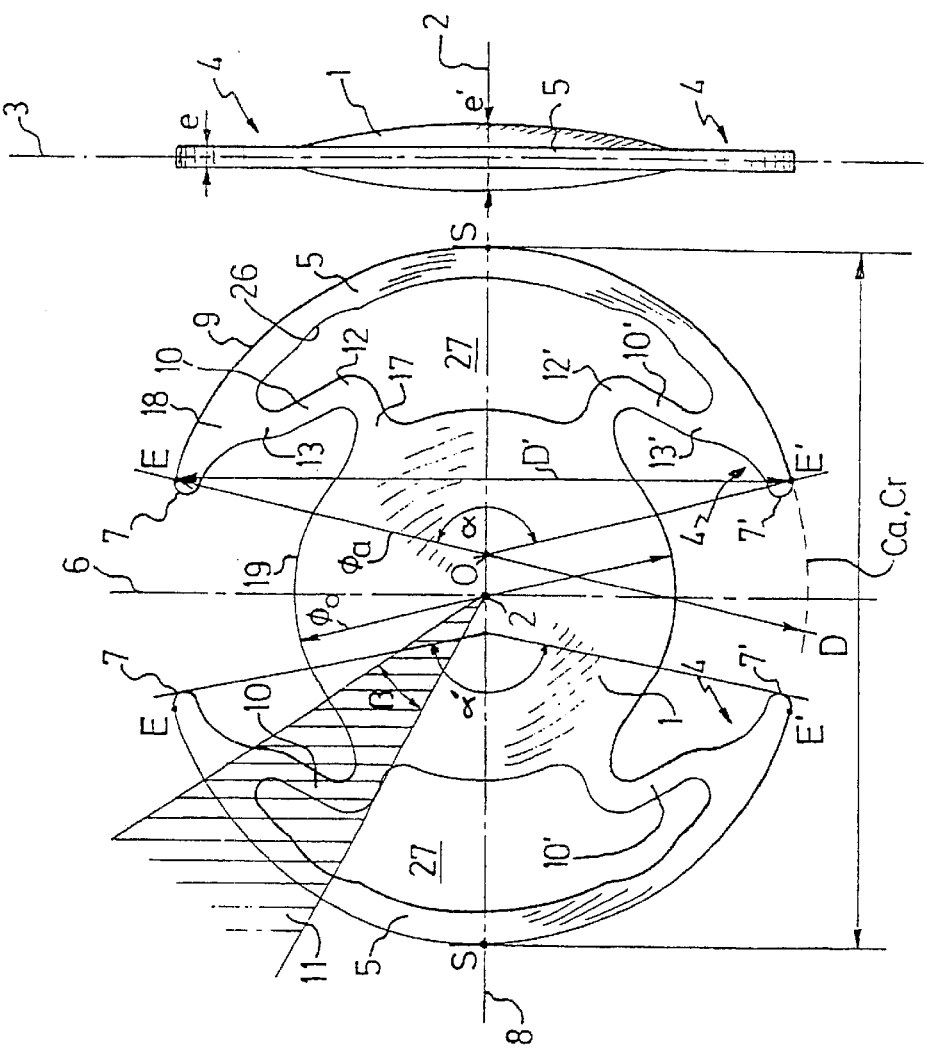

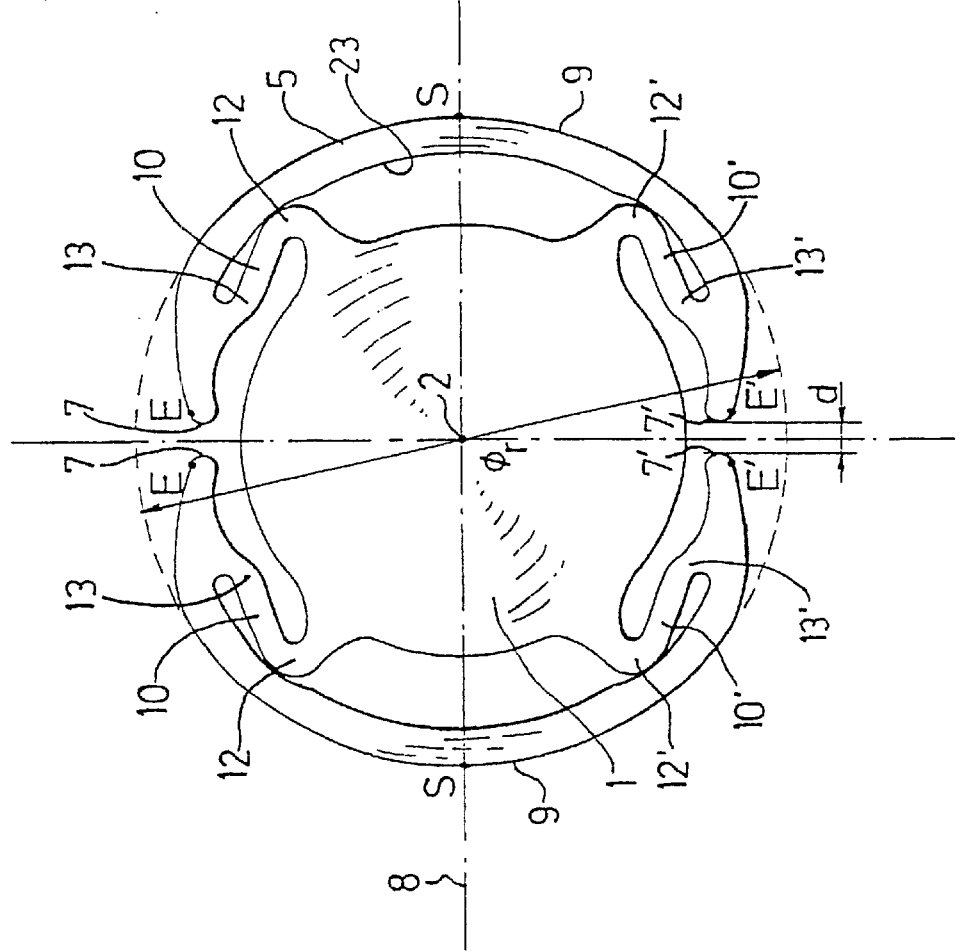

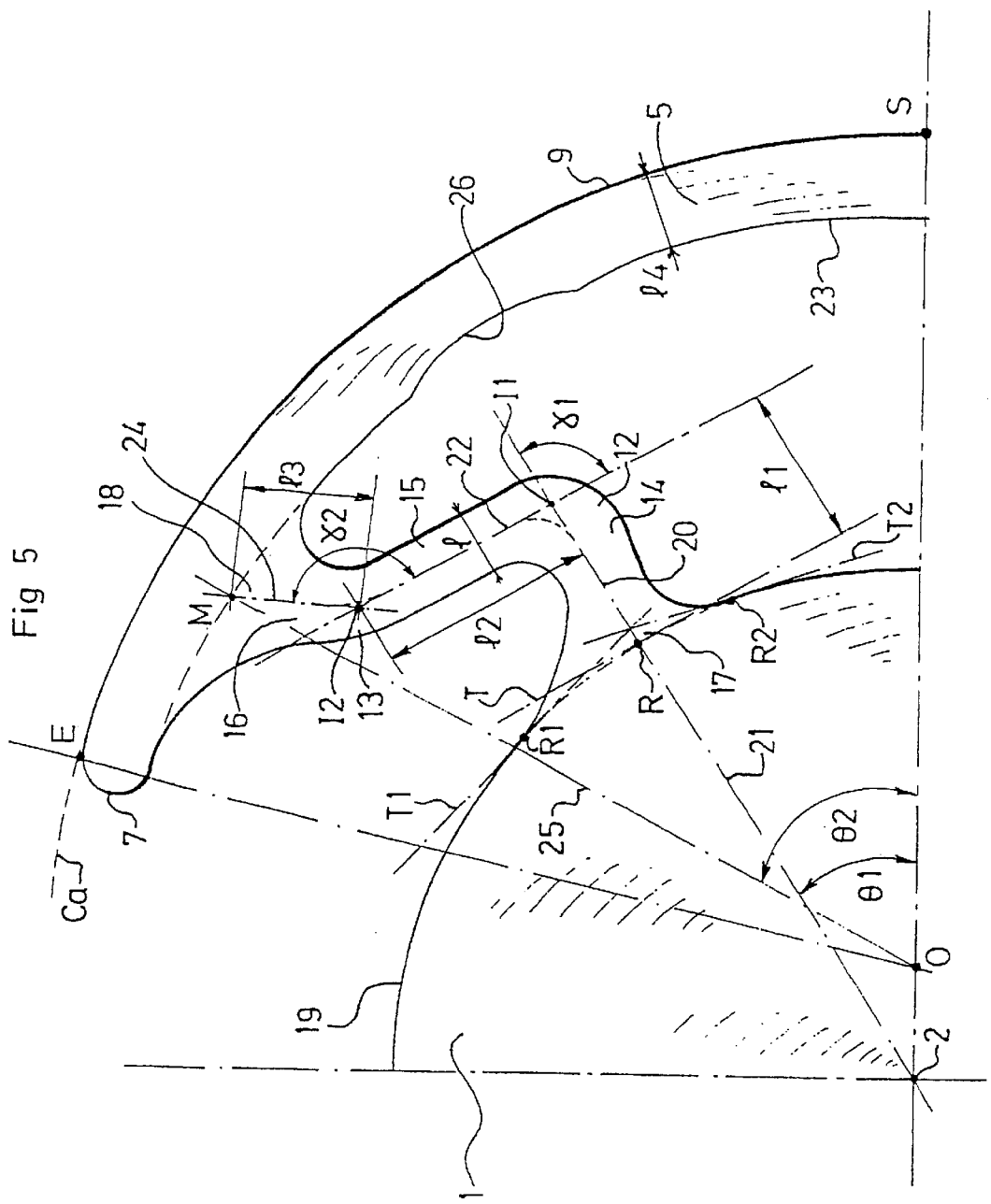

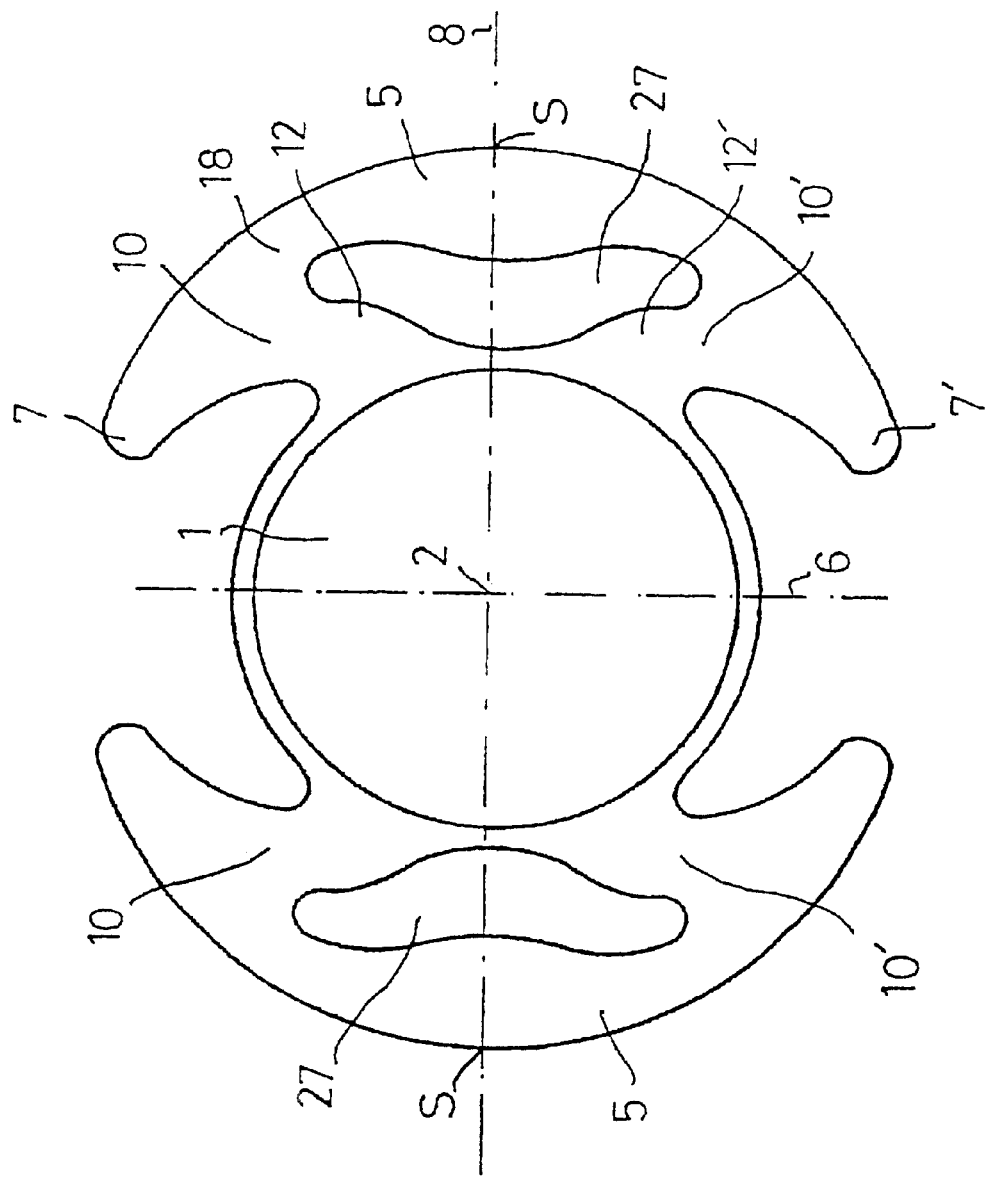

FLEXIBLE MONOBLOC INTRAOCULAR LENS

FIELD OF THE INVENTION

The invention concerns a monobloc intraocular lens made of a flexible material which can be rolled or folded, but which is sufficiently elastic for the lens to regain, after being implanted in an ocular housing, a functional shape corresponding to its initial shape, namely exhibiting a shape memory.

BACKGROUND OF THE INVENTION

Former generations of intraocular lenses were made of a rigid material (such as PMMA) and, in order to be implanted in the eye, a large incision had to be made in the cornea (usually of the order of 6 mm corresponding to the diameter of the optic part of the lens) which presented many disadvantages (post-operative astigmatism, greater risks of surgical complications etc).

In order to overcome these disadvantages, lenses have been proposed made of a flexible material such as silicone or materials described as "hydrogels", or "acrygel", or "acrylic" (this term having a different meaning from its common one) which are PMMAs (polymethylmethacrylate) and/or HEMA (hydroxyethylmethacrylate) hydrated to more than 16%, in particular between 24% and 28%. These lenses can be folded or rolled and can be implanted through a smaller incision, in particular through the incision made in order to introduce an instrument into the eye necessary for prior surgical treatment (for example a 3 mm to 3.5 mm incision for ablation of the crystalline lens by phacoemulsification).

Nevertheless, the flexibility of this material then presents the problem of the mechanical stability of the lens after implantation. In particular, in the case of capsular lenses, since the capsular sac has initially a diameter of the order of 10 to 11.5 m, it retracts radially after ablation of the crystalline lens, to a diameter of the order of 9.5 mm or even less.

In order to oppose this retraction, bicomponent lenses have been proposed of which the optic part is flexible while the haptic parts are made of rigid PMMA. These lenses have a complex structure and there is a risk of their flexible optic part deforming under the effect of radial stresses transmitted by the rigid haptic parts.

On the other hand, monobloc lenses have been proposed made of a flexible material, designed to be adapted to radial deformations of the ocular housing. In particular, monobloc lenses are known (EP-579 528) made of a flexible material comprising a central optic part in the shape of a disc defining a principal plane of the lens and a haptic part comprising:

two loops, so-called contact loops, designed to come into contact with an inner wall of the eye, each of these contact loops having the general shape of a convex circular arc, with a convexity directed outwards radially with respect to the optic part, these contact loops being both inscribed in the same circle with a diameter of the order of 11 mm, for each contact loop, two linking elements extending between the optic part and the contact loop, the lens having, seen in plan, and before implantation, an initial shape which is symmetrical overall with respect to the two perpendicular axes of symmetry contained within the principal plane.

Nevertheless, phenomena of angular displacements (tilt) and/or axial displacements and/or radial displacements (eccentricity) and/or deformations, in particular bending movements, are also sometimes noticed with these lenses after implantation.

Certain monobloc lenses have also been proposed having the haptic parts tilted with respect to the principal plane of the optic part, so that deformations can occur in flexion perpendicular to this principal plane. Nevertheless, with these lenses, the risk of premature displacement and/or deformation phenomena is not overcome. Moreover, these tilted lenses present a not inconsiderable risk of error in positioning the axial direction. Indeed, the relatively small direction of tilt is virtually undetectable by the surgeon, taking into account in particular the flexibility of the material. In addition, since the lens is folded and/or rolled when implanted, an error is possible in assessing the direction of deployment of the lens.

SUMMARY OF THE INVENTION

The object of the invention is to overcome these disadvantages, by providing a monobloc intraocular lens made of a flexible material with a shape memory which can adapt to radial retraction of the ocular housing in which it is implanted without risk of premature displacements or deformations of the optic part.

The object of the invention is more particularly to provide a monobloc intraocular lens of which the haptic part is deformable radially so as to be adapted to the radial retraction of the ocular housing, in particular for the capsular sac with a value of the diameter of the order of 9.5 mm, but which can reach a diameter of the order of 8.5 mm, the optic part remaining in the same principal plane, the symmetries of the lens being at least substantially preserved during deformations of the haptic art (under the effect of stresses which are assumed to be uniformly distributed), the optic part remaining centred on the same axis and not undergoing perceptible deformation affecting its optical properties.

The object of the invention is also to provide a lens which is, and remains, perfectly stable in the ocular implantation housing.

The object of the invention is also to provide a lens which can be easily inserted and in particular may be inserted through a smaller incision, in particular 3 to 3.5 mm, the lens being folded and/or rolled, and without the risk of error in the axial direction in which the lens is inserted by the surgeon.

The object of the invention is also to provide a lens which is simple and inexpensive to produce.

The object of the invention is more particularly to provide a posterior chamber lens, in particular a capsular lens, namely one intended to be implanted in the capsular sac or a lens intended to be implanted in the sulcus.

The object of the invention is also to provide a lens which can be applied to an adult as well as to a child.

To this end, the invention concerns a monobloc intraocular lens made of a flexible material which can be folded or rolled, but which is sufficiently elastic so that the lens regains, after being implanted in an ocular housing with a mean diameter equal to φm, a functional shape corresponding to its initial shape, comprising a central optic part in the shape of a disc having an optical axis and defining a principal plane of the lens perpendicular to the optical axis, and a haptic part comprising two loops in contact with an inner wall of the eye, each of these contact loops having an external surface with a generally convex-shaped curve with a convexity directed outwards radially with respect to the optic part, for each contact loop, two linking elements extending between the optic part and the contact loop, the lens having, seen in plan, and before implantation, an initially overall symmetrical shape with respect to the two perpendicular axes of symmetry contained within the principal plane, the so-called horizontal principal axis and vertical principal axis, the external surface of each contact loop having a trace in the principal plane which is a convex curve defining an apex of intersection with the horizontal principal axis, and two points, referred to as end points, equidistant from the horizontal principal axis between which the radius of curvature is always greater than 2.5 mm, wherein:

the circle passing through the apex and the two end points of each contact loop has a diameter $\phi a$ greater than or equal to $\phi m$ and less than $\phi m+1.5$ mm, the apices of the two contact loops are separated from each other by a distance D different from $\phi a$ and greater than $\phi a$, the linking elements are adapted so that they can be deformed in flexion in the principal plane in the direction of a reduction in the radial dimensions of the lens by bringing the contact loops towards each other and the optic part, while preserving the symmetry of the lens with respect to the two horizontal and vertical principal axes, and at least substantially without deformation or displacement of the optic part, so that the lens can be adapted to a radial retraction of the ocular housing.

In all the text, unless indicated to the contrary, the described geometrical or dimensional characteristics of the lens are those which it has before implantation, i.e. those which correspond d to its initial shape. The lengths and widths are dimensions parallel to the principal plane and the thicknesses are dimensions perpendicular to the principal plane, i.e. parallel to the optical axis of the optic part. "Trace of a surface in the principal plane" is understood to mean the curve of intersection of this surface and the principal plane.

Advantageously and according to the invention, the contact loops and the linking elements are adapted so that the contact loops can be brought towards each other and the optic part so that the trace of the external surface of the contact loops in the principal plane is circumscribed in a circle with a diameter $\phi r$ less than or equal to $\phi a$ and greater than $\phi m-1$ mm.

Advantageously and according to the invention, each linking element has at least one elbow in the principal plane, and in particular at least one elbow with a convexity directed towards the contact loop, and is adapted so as to be deformable in flexion in the principal plane with a bending axis passing through this elbow. More particularly, advantageously and according to the invention, each linking element has at least one first elbow with a convexity directed towards the contact loop, and at least one second elbow with a concavity directed towards the contact loop.

Advantageously and according to the invention, each linking element is formed of at least one strand of material, referred to as a linking strand, with a width at least substantially constant and a thickness at least substantially constant, and extending between a junction zone with the periphery of the optic part and a junction zone with a contact loop while having at least one elbow in the principal plane. More particularly, advantageously and according to the invention, each linking element is formed of a single linking strand having at least one first elbow with a convexity directed towards the contact loop.

Advantageously and according to the invention, the junction zone of a linking strand with the periphery of the optic part is disposed at least substantially in the extension of a radius of the optic part, this radius forming with the horizontal principal axis, an angle of between 20° and 45° in particular of the order of 30°. Moreover, advantageously and according to the invention, each linking strand is linked to a contact loop in a junction zone disposed on a radius of the circle passing through the apex and the two end points, forming with the horizontal principal axis an angle of between 45° and 75°, in particular of the order of 60°. In addition, advantageously and according to the invention, each linking element is inscribed in an angular sector of which the centre corresponds to that of the optic part and is at least substantially a bisector of the two principal horizontal and vertical axes.

Advantageously and according to the invention, the contact loops and the linking elements extend at least substantially over the principal plane, the lens having zero tilt. Moreover, advantageously and according to the invention, each contact loop is formed of a curved arc with a width which is at least substantially constant extending between the two free ends.

Advantageously and according to the invention, the trace of the external surface of each contact loop in the principal plane is a portion of a circle of diameter $\phi a$. As a variant, this trace may be distinct from a circle and may have a radius of curvature which varies between the apex and the end points, for example it may be conical.

It should be noted that in the prior art, attempts have been made up to now to cause isotropic radial deformations, i.e. those substantially of the same value over all the contact surface of the haptic part with the internal walls of the ocular housing.

On the contrary, in the invention, deformations of the lens include a bringing together in translation of the two contact loops along a preferred direction, namely the horizontal principal axis, on account of the fact that $D>\phi a$. It has been proved that this characteristic enables much greater deformation amplitudes to be obtained in practice, which makes it possible to adapt to the capsular retraction, whatever its extent, preventing in this way displacements and deformations of the optic part.

The invention also concerns a lens characterized in combination by all or part of the characteristics mentioned above or hereinafter.

BRIEF DESCRIPTION OF THE DRAWINGS

Other objects, characteristics and advantages of the invention will become apparent on reading the following description of its preferred embodiments shown in the accompanying figures, in which:

FIG. 1 is a plan view of a lens according to one embodiment of the invention,

FIG. 2 is a side view of the lens of FIG. 1,

FIG. 3 is a plan view of the lens of FIG. 1 in the deformed state, circumscribed in a cylindrical template of diameter $\phi r$, FIG. 4 is side view of the lens of FIG. 3, FIG. 5 is a detailed plan view of an upper right hand quarter of the lens of FIG. 1, FIGS. 6 and 7 are partial plan views illustrating respectively two alternative embodiments of the lens according to the invention, FIG. 8 is view similar to FIG. 1 illustrating another alternative embodiment of a lens according to the invention.

DETAILED DESCRIPTION OF THE INVENTION

Figure 6:
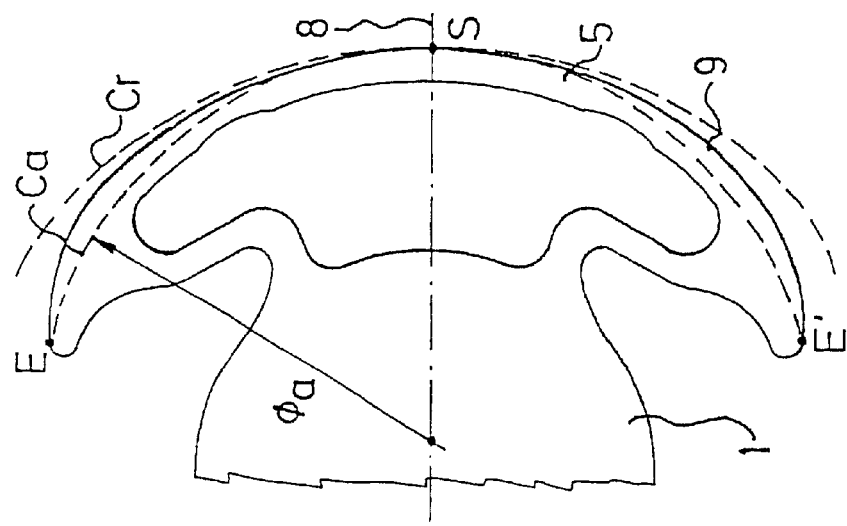

A lens according to the invention shown in the figures includes an optic part 1 with a generally disc-shape with a diameter φo of between 5 and 7 mm, in particular equal to 6 mm, having in the example shown, two convex surfaces so as to have a suitable optical power. The central axis 2 of this disc is the optical axis of the optic part 1.

The lens extends overall over a principal plane 3 perpendicular to this optical axis 2. In the embodiments shown, the principal plane 3 is a central plane of symmetry of the lens. The lens additionally includes a haptic part 4 designed to come into contact with the inner walls of an ocular housing in which the lens must be implanted, this haptic part 4 having the function of holding the optic part 1 in place in the ocular housing.

The lens is a monobloc, i.e. it consists overall of a single piece of a flexible material which can be folded or rolled, but which is sufficiently elastic so that the lens regains, after being implanted in the ocular housing, a functional shape corresponding to its initial shape, i.e. having a shape memory. This material is for example a hydrogel.

The ocular housing in which the lens must be implanted has a mean diameter φm well known to eye specialists. This mean diameter is the median value of the range of values of natural diameters encountered, according to the subjects, in an implantation situation, i.e. after any possible surgical treatment that may be previously carried out. In other words, the mean diameter φm is the most probable diameter of the ocular housing which must receive the lens.

In particular, the mean diameter φm of the capsular sac after ablation of the crystalline lens (cataract operation) and post-operative contraction is 9.5 mm in an adult, (where this diameter varies from 9 mm to 10 mm) and 8.5 mm in a child (where this diameter varies from 8 mm to 9 mm). It should be noted that the mean diameter is considered after radial retraction of the ocular housing brought about by any possible surgical treatment.

In a similar manner, the mean diameter φm is equal to 12 mm if the ocular housing considered is the sulcus (adult).

The haptic part 4 includes two diametrically opposed contact loops 5 either side of the optic part 1, symmetrical with each other with respect to a diametral axis of symmetry of the optic part 1, referred to as a vertical principal axis 6, contained within the principal plane 3. In all the text, the same references are used to denote similar elements which are symmetrical with respect to the vertical principal axis 6.

Each contact loop 5 is formed of a curved arc with a width 14 at least substantially constant extending between two free ends 7,7'. This width 14 is for example of the order of 0.5 mm. Each contact loop 5 has a generally symmetrical shape with respect to a diametral axis of symmetry 8 of the optic part 1, referred to as the horizontal principal axis 8, contained within the principal plane 3 and perpendicular to the vertical principal axis 6.

The contact loops 5 have a convex-shaped curve with a convexity directed outwards radially with respect to the optic part 1, and have an external surface 9 designed to come into contact with an internal wall of the ocular implantation housing. The trace of this external surface 9 in the principal plane 3 is a convex curve defining an apex S of intersection with the horizontal principal axis 8, and extending between two end points E, E' equidistant from the horizontal principal axis with a radius of curvature greater than 2.5 mm.

This radius of curvature may or may not be constant between the apex S and each end point E, E'. In the preferred embodiment shown in FIGS. 1 to 5, this radius of curvature is constant and the trace in the principal plane 3 of the external surface 9 of each contact loop 5 is a portion of a circle of diameter φa.

Figure 7:
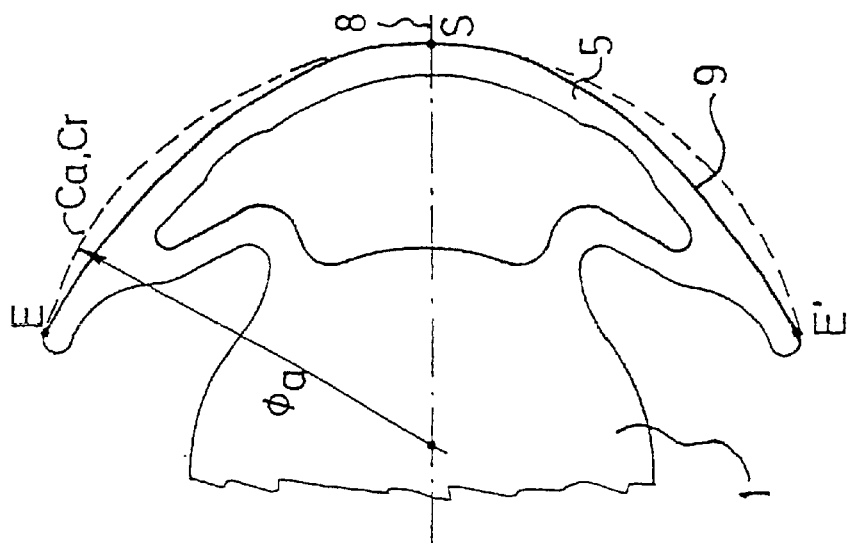

In the variants of FIGS. 6 and 7, the radius of curvature varies from the apex S to the end point E, E'. In other words, the value of the radius of curvature at the apex S is different from its value at the end points E,E'. This radius of curvature exhibits a monotonic variation (it is either always increasing (FIG. 6) or always decreasing (FIG. 7)) between the apex S and each end point E,E'. Advantageously, the trace in the principal plane 3 of the external surface 9 of each contact loop 5 is a conical portion of a curve. In the variant of FIG. 6, a curve has been shown for example having a minimum radius of curvature at the apex S and which increases to the end points E,E'. This curve is for example a portion of a parabola or a hyperbola. In the variant of FIG. 7, the radius of curvature is a maximum at the apex S and decreases to the end points E,E'. This curve is for example an ellipse.

In all cases, one and only one circle Ca exists for each contact loop 5, passing through the apex S and the two end points E, E', the diameter of which is φa.

Each contact loop 5 is connected to the optic part 1 by two linking elements 10, 10', symmetrical with each other with respect to the horizontal principal axis 8 and extending between the circular periphery 19 of the optic part 1 and the contact loop 5. The lens thus includes four linking elements 10, 10'. The contact loops 5 and the linking elements 10, 10' extend at least substantially over the principal plane 3, the lens having zero tilt.

The lens has, seen along the principal plane 3, an overall symmetrical shape with respect to the two vertical 6 and horizontal 8 principal axes. In other words, it may be generated by the symmetry from a quadrant with respect to these axes in order to obtain the three other quadrants. Only one quadrant is shown in FIG. 5 in greater detail.

According to the invention,
the circle Ca passing through the apex S and the two end points E, E' of each contact loop 5 has a diameter φa greater than or equal to φm and less than φm+1.5 mm,
the apices S of the two contact loops are separated from each other by a distance D different from φa and greater than φa,
the linking elements 10, 10' are adapted so that they can be deformable in flexion in the principal plane 3 in the direction of a reduction in the radial dimensions of the lens by bringing the contact loops 5 towards each other and the optic part 1, in translation along the direction of the horizontal principal axis 8, while preserving the symmetry of the lens with respect to the two horizontal 8 and vertical 6 principal axes, and at least substantially without deformation or displacement of the optic part 1, so that the lens can be adapted to a radial retraction of the ocular housing.

More particularly, the contact loops 5 and the linking elements 10, 10' are adapted so that the contact loops 5 can be brought towards each other and the optic part 1 so that the lens can be circumscribed in a cylindrical template of diameter φr, and so that the trace of the external surface 9 of the contact loops 5 in the principal plane 3 is circumscribed in a circle Cr of diameter φr, this diameter φr being less than φa and greater than φm−1 mm (FIG. 3).

Advantageously and according to the invention, φa is different from φm. In this way, the deformation of the haptic part 4 under the effect of a radial contraction of the ocular housing is accompanied by a reduction in the diameter of the circle Ca, the radius of curvature of the contact loops 5 reducing. Advantageously and according to the invention, φa is greater than or equal to φm+0.2 mm and less than or equal to φm+0.7 mm, and is in particular of the order of φm+0.5 mm.

Particularly in the case of a capsular lens, φa lies between 8.5 and 11 mm. When the capsular lens is intended to be implanted in an adult male, φa is greater than or equal to 9.5 mm and less than or equal to 10.5 mm, and is in particular of the order of 10 mm. When it is intended to be implanted in a child, φa is greater than or equal to 8.5 mm and less than or equal to 9.5 mm, and is in particular of the order of 9 mm.

In addition, advantageously and according to the invention, D is greater than or equal to φa+1 mm and less than or equal to φa+2 mm. Preferably, particularly in the case of a capsular lens, D is greater than or equal to φm+1.5 mm and less than or equal to φm+2.5 mm. Advantageously and according to the invention, for a capsular lens (for an adult or a child), D lies between 11 mm and 12 mm, and is in particular of the order of 11.2 mm.

In the case of a lens intended to be implanted in the sulcus, advantageously and according to the invention, φa lies between 12 mm and 13.5 mm, and is in particular of the order of 12.5 mm, and D lies between 13 mm and 14 mm, and is in particular of the order of 13.5 mm.

During a radial deformation in compression under the effect of the radial retraction of the ocular housing, the two apices S become closer together while remaining on the horizontal principal axis 8 and the diameter of the circle Ca passing through the apex S and the end points E, E' of each contact loop 5 reduces in diameter, from φa to a value which may be of the order of φm, or even less than φm, as far as φm−1 mm. The circle Ca is centred on a point O of the horizontal principal axis 8 which is approximately 0.6 mm away from the optical axis 2.

The enveloping circle Cr which circumscribes the trace of the external surface 9 has a diameter greater than φa (variant of FIG. 7) or equal to φa (variants of FIGS. 1 to 6) before deformation of the lens. In the variants of FIGS. 1 to 6, when the radius of curvature at the apex S is less than or equal to that at the end points E, E', the enveloping circle Cr and the circle Ca passing through the apex S and the end points E, E' are coincident.

In the deformed state (FIGS. 3 and 4) the lens is circumscribed in the enveloping circle Cr of which the diameter φr has decreased. Advantageously and according to the invention, the lens is adapted so that φr can take any value between φm−1 mm and φa.

During a deformation, the distance D between the apices S of the contact loops decreases and the diameters of the circles Ca and Cr decrease.

Advantageously and according to the invention, the lens is adapted so that when φr=φm, D=φr=φm, i.e. the enveloping circles Cr of the two contact loops 5 are coincident and centred on the axis 2 of the optic part 1 as shown in FIG. 3.

In addition, advantageously and according to the invention, each contact loop 5 extends between the two end points E, E' over an angular sector defined by the circle Ca passing through the apex S and the two end points E, E', with an angle α greater than or equal to 60° and less than 180°. More particularly, advantageously and according to the invention, the angle a lies between 90° and 150°.

Similarly, each contact loop 5 extends between its two free ends 7, 7' over an angular sector centred on the centre 0 of the circle Ca, with an angle α' greater than or equal to 60° and less than 180°, in particular between 90° and 160°. Advantageously and according to the invention, the angle α' is adapted so that the two contact loops 5 cannot butt up against each other. More precisely, the angle α' is adapted so that the two contact loops 5 have, in the deformed state of the lens, free ends 7, 7' facing each other at a distance apart from each other d of between 0.1 mm and 1 mm, in particular of the order of 0.5 mm (FIG. 3). As a variant (not shown) it is also possible to provide for the angle α' to be adapted so that the facing free ends 7, 7' butt up against each other (d=0 mm) at least from a certain deformation in radial compression, in particular in a deformed state for which D=φr≧φm.

Advantageously and according to the invention, each linking element 10, 10' is inscribed in an angular sector 11 of which the centre corresponds to that of the optic part 1 and which is at least substantially a bisector of the two horizontal 8 and vertical 6 principal axes. This angular sector 11 is hatched in FIG. 1 and extends over an angle β of between 20° and 40°, in particular of the order of 30°.

In the embodiments shown, the lens is an implant in the general shape of a disc, a so-called "disc implant". Accordingly, the distance D' between E and E', namely the chord subtending the external surface 9 of the contact loop is greater than the diameter φo of the optic part 1. It should be noted that the invention would also apply in the case where the distance D' between E and E' would be less than or equal to φo, the lens then being an implant of the so-called "shuttle implant" type.

In addition, advantageously and according to the invention, each linking element 10, 10' has at least one elbow 12, 12', 13, 13' in the principal plane 3 and is adapted so as to be deformable in flexion in the principal plane 3 with a bending axis passing through this elbow 12, 12', 13, 13'. More particularly, each linking element 10, 10' has at least one first elbow 12, 12' with a convexity directed towards the contact loop 5, and at least one second elbow 13, 13' with a concavity directed towards the contact loop 5. It would be possible to provide linking elements 10, 10' including strands of material in a serpentine shape, namely with more than two elbows. Nevertheless, in the embodiments shown, preferably and according to the invention, each linking element 10, 10' includes a single first elbow 12, 12' with a convexity directed towards the contact loop 5, and a single second elbow 13, 13' with a concavity directed towards the contact loop 5.

Each linking element 10, 10' is formed of at each one strand of material, a so-called linking strand, with a width l at least substantially constant and with a thickness e at least substantially constant, and extending between a junction zone 17 with the periphery 19 of the optic part 1 and a junction zone 18 with a contact loop 5 while having at least one elbow 12, 12', 13, 13' in the principal plane 3. Preferably, each linking element 10, 10' is formed of a single linking strand having at least one first elbow 12, 12' with a convexity directed towards the contact loop 5. Nothing however will prevent several distinct linking strands from being provided for each linking element 10, 10', i.e. for linking the optic part 1 to each contact loop 5 on each side of the principal axis 8, for example a first linking strand having an elbow with a convexity directed towards the contact loop 5, and a second linking strand having an elbow with a concavity directed towards the contact loop 5.

A linking element 10 is shown in greater detail in FIG. 5. It comprises a linking strand 10 including a first segment 14 which is at least substantially straight, extending from the optic part 1, and a second segment 15 which is at least substantially straight, extending from the first segment 14, forming therewith a first elbow 12 with a convexity directed towards the contact loop 5, this second segment 15 being connected to the contact loop 5. The first elbow 12 defines an angle γ1 between the first segment 14 and the second segment 15 of between 60° and 120°, in particular of the order of 90°.

The convexity of the first elbow 12, 12' is also directed towards the apex S, i.e. towards the horizontal principal axis 8. The second segment 15 extends at least substantially parallel to a straight line T tangential to the periphery 19 of the optic part 1 in the junction zone 17 of the first segment 14 with the optic part 1. The junction zone 17 with the periphery 19 of the optic part extends between two connecting fillet points R1, R2 of the first segment 14. The second segment 15 extends along a direction which is parallel to one of the tangents to the peripheral circle 19 of the optic part 1 between these connecting points R1 and R2, i.e. which is directed between the directions of the tangents T1 and T2 respectively at these points R1 and R2 on the peripheral circle 19. More particularly, a middle line 20 of the first segment 14 can be defined, independent of the fillets. This middle line 20 intersects the peripheral circle 19 of the optic part 1 at a point R where a tangent T may be drawn to the circle 19. The second segment 15 is at least substantially parallel to this tangent T.

In addition, the first segment 14 extends at least substantially radially from the periphery 19 of the optic part 1. Accordingly, the middle line 20 is at least substantially in the extension of a radius 21 of the peripheral circle 19 of the optic part 1, centred on the optical axis 2. This radius 21 forms an angle $\theta 1$ with the horizontal principal axis 8 which lies between 20° and 45°, in particular of the order of 30°. Accordingly, the junction zone 17 of a linking strand 10, 10' to the periphery 19 of the optic part 1 is disposed at least substantially in the extension of a radius 21 of the periphery 19 of the optic part 1 forming with the horizontal principal axis 8, an angle $\theta 1$ of between 20° and 45°, in particular of the order of 30°.

The second segment 15 also includes a middle line 22. The middle line 20 of the first segment 14 and the middle line 22 of the second segment 15 intersect at a point I1 and form between them the angle $\gamma 1$ of the first elbow 12.

Each linking strand 10, 10' includes a third segment 16 linking the second segment 15 to the contact loop 5 and forming, with the second segment 15, a second elbow 13 with a concavity directed towards the contact loop 5. The second elbow 13 defines an angle $\gamma 2$ between the second segment 15 and the third segment 16 of between 120° and 160°, in particular of the order of 140°. The third segment 16 is connected to the contact loop 5 in a junction zone 18, by connecting fillets. The contact loop 5 has a concave curved internal surface 23 parallel to the external surface 9. The third segment 16 is connected to the internal surface 23 of the contact loop 5. Independently of the connecting fillets, the third segment 16 includes a middle line 24 which intersects the middle line 22 of the second segment 15 at a point I2, while forming between them the angle $\gamma 2$. The middle line 24 intersects the trace of the internal surface 23 at a point M.

The second segment 15 has a length l2 (distance (I1, I2)) greater than that, l1, of the first segment 14 (distance I1, R)). The length l2 of the second segment lies between 1 mm and 3 mm, in particular of the order of 1.5 mm, whereas the length l1 of the first segment 14 lies between 0.5 mm and 1 mm, in particular of the order of 0.75 mm.

In addition, the length l3 of the third segment 16 (distance I2, M)) is also less than that l2 of the second segment 15, and lies between 0.2 mm and 1 mm, in particular of the order of 0.6 mm.

The second segment 15, and more generally all the linking strand 10, apart from the connecting fillets, has a width l which is at least substantially constant and of the order of 0.5 mm.

Moreover, the thickness e of each linking strand 10 is at least substantially constant, and is the same as the thickness of the contact loop 5. The entire haptic part 4 thus has the same thickness e. This thickness e is less than the overall thickness e', in the region of the optical axis 2, of the optic part 1 (FIG. 2). The thickness e advantageously lies between 0.2 mm and 0.4 mm and is in particular of the order of 0.25 mm.

The junction zone 18 of the linking strand 10 with the contact loop 5 is disposed at least substantially in the extension of a radius 25 of the circle Ca passing through the apex S and the two end points E, E'. This radius 25 forms, with the horizontal principal axis 8, an angle $\theta 2$ of between 45° and 75°, in particular of the order of 60°.

During a deformation of the lens in radial compression, the linking strands 10, 10' flex in the closing direction of the angle $\gamma 1$ of the first elbow 12, 12' and in the opening direction of the angle $\gamma 2$ of the second elbow 13,13'.

Taking into account the symmetry of the lens with respect to the horizontal principal axis 8, in the undeformed state of the lens, the second segments 15 of the two linking strands 10,10' of at least one contact loop 5 extend, from the first elbow 12,12' overall while moving away from each other and from the horizontal principal axis 8. During the deformation of the linking strands 10, 10' the second segments 15 move in rotation (flexion) in opposite directions of rotation, while approaching the horizontal principal axis 8.

It should be noted that the direction of flexing of each linking strand 10,10' in the region of the first elbows 12,12' with a convexity directed towards the contact loop 5, is the same as the direction of flexing of the portion of the contact loop 5 to which this linking strand 10,10' is connected.

FIG. 3 shows an extreme deformation position in which the first elbows 12,12' come into contact, butted up against the internal surface 23 of the contact loops 5. Advantageously, cutaways 26 are provided hollowed out in the internal surface 23 so as to reduce the minimum permissible value of the diameter $\phi r$.

During deformations of the lens, the haptic part 4 (linking elements 10, 10' and contact loops 5) remain in the principal plane 4, and the symmetry of the lens with respect to the two horizontal 8 and vertical 6 principal axes is preserved. The linking elements 10, 10' flex without opposing any substantial resistance, taking into account the high leverage represented by the second and third segment 15, 16 (between I1 and M) from the first elbow 12, 12' . In this way, the optic part 1 is subjected to few stresses and is not substantially deformed.

It should be noted that the lens according to the invention is very easily manufactured at low cost, for example by milling a block of hydrogel with aid of a 0.4 mm diameter milling cutter.

FIGS. 1 to 4 show, on an enlarged scale, an actual example of a capsular lens for an adult ($\phi m=9.5$ mm) according to the invention in which $\phi o=6$ mm, D=11.2 mm, $\phi a=10$ mm, $\phi r=9$ mm and $\alpha=150°$. No displacement or deformation of the optic part 1 is noted in the deformed state.

In the embodiments shown in FIG. 1 to 7, each linking element 10, 10' is linked to a contact loop 5 in the vicinity of, but away from, one of its free ends 7, 7', the contact loop 5 being extended beyond the junction zone 18 with the linking element 10, 10'.

In the variant of FIG. 8, each linking element 10, 10' is linked to the end 7, 7' of the contact loop 5. Moreover, in the variant, the linking elements 10, 10' have a width which increases continually from the elbow 12, 12' towards the contact loop 5.

Moreover, the width of the contact loop 5 is greater in the region of the apex S and the horizontal principal axis 8. It increases continually from the junction zone 18 of the linking element 10, 10' towards the apex S.

The opening 27 formed between the optic part 1, a contact loop 5 and the two linking elements 10, 10' of this contact loop is smaller in the variant of FIG. 8 than in the embodiments of FIGS. 1 to 7.

With the lens according to the invention, it should be noted that area of the contact surface with the enveloping circle Cr, and thus with the internal walls of the ocular housing (capsular sac) in the deformed state of the lens, is very large. The lens according to the invention therefore makes it possible to prevent the so-called secondary cataract phenomenon, such a peripheral contact surface limiting cellular proliferation.

Moreover, the lens according to the invention make be inserted, folded and rolled, through an incision made for the passage of the phaco-emulsification instrument without any error in the direction of insertion, the lens not being tilted.

What is claimed is:

1. A monobloc intraocular lens made of a flexible material which can be folded or rolled, but which is sufficiently elastic so that the lens regains, after being implanted in an ocular housing with a mean diameter equal to $\phi m$, a functional shape corresponding to its initial shape, comprising a central optic part (1) in the shape of a disc having an optical axis (2) and defining a principal plane of the lens (3) perpendicular to the optical axis (2), and a haptic part (4) comprising two loops (5) adapted to contact with an inner wall of the eye, each of these contact loops (5) having an external surface (9) with a generally convex-shaped curve with a convexity directed outwards radially with respect to the optic part (1), for each contact loop (5), two linking elements (10, 10') extending between the optic part (1) and the contact loop (5), the lens having, seen in plan, and before implantation, an initially overall symmetrical shape with respect to two perpendicular axes of symmetry contained within the principal plane (3), the so-called horizontal principal axis (8) and vertical principal axis (6), the external surface (9) of each contact loop (5) having a trace in the principal plane (3) which has a generally convex-shaped curve defining an apex (S) of intersection with the horizontal principal axis (8), and two points, referred to as end points (E, E'), equidistant from the horizontal principal axis (8) between which the radius of curvature is always greater than 2.5 mm, wherein:

the circle (Ca) passing through the apex (S) and the two end points (E, E') of each contact loop (5) has a diameter $\phi a$ greater than or equal to $\phi m$ and less than $\phi m+1.5$ mm, the apices (S) of the two contact loops (5) are separated from each other by a distance D different from $\phi a$ and greater than $\phi a$, the linking elements (10, 10') are adapted so that they can be deformed in flexion in the principal plane (3) in the direction of a reduction in the radial dimensions of the lens by bringing the contact loops (5) towards each other and the optic part (1), while preserving the symmetry of the lens with respect to the two horizontal (8) and vertical (6) principal axes, and at least substantially without deformation or displacement of the optic part (1), so that the lens can be adapted to a radial retraction of the ocular housing.

2. A lens as claimed in claim 1, wherein the contact loops (5) and the linking elements (10, 10') are adapted so that the contact loops (5) can be brought towards each other and the optic part (1) so that the trace of the external surface (9) of the contact loops (5) in the principal plane (3) is circumscribed in a circle Cr with a diameter $\phi r$ less than or equal to $\phi a$ and greater than $\phi m-1$ mm.

3. A lens as claimed in claim 1, wherein each linking element (10, 10') has at least one elbow (12, 12', 13, 13') in the principal plane (3) and is adapted so as to be deformable in flexion in the principal plane (3) with a bending axis passing through this elbow (12, 12', 13, 13').

4. A lens as claimed in claim 3, wherein each linking element (10, 10') has at least one first elbow (12, 12') with a convexity directed towards the contact loop (5), and at least one second elbow (13, 13') with a concavity directed towards the contact loop (5).

5. A lens as claimed in claim 1, wherein each linking element (10, 10') is formed of at least one strand of material, referred to as a linking strand, with a width (l) at least substantially constant and a thickness (e) at least substantially constant, and extending between a junction zone (17) with the periphery (19) of the optic part (1) and a junction zone (18) with a contact loop (5) while having at least one elbow (12, 12', 13, 13') in the principal plane (3).

6. A lens as claimed in claim 5, wherein each linking element (10, 10') is formed of a single linking strand having at least one first elbow (12, 12') with a convexity directed towards the contact loop (5).

7. A lens as claimed in claim 5, wherein each linking strand (10, 10') includes a first segment (14) which is at least substantially straight, extending from the optic part (1), and a second segment (15) which is at least substantially straight, extending from the first segment (14), forming therewith a first elbow (12) with a convexity directed towards the contact loop (5), this second segment (15) being connected to the contact loop (5).

8. A lens as claimed in claim 7, wherein the first elbow (12) defines an angle ($\gamma$1) between the first segment (14) and the second segment (15) of between 60° and 120°.

9. A lens as claimed in claim 7, wherein the second segment (15) extends at least substantially parallel to a straight line (T) tangential to the periphery (19) of the optic part (1) in the junction zone (17) of the first segment (14) with the optic part (1).

10. A lens as claimed in claim 7, wherein the first segment (14) extends at least substantially radially from the periphery (19) of the optic part (1).

11. A lens as claimed in claim 7, wherein each linking strand (10, 10') includes a third segment (16) linking the second segment (15) to the contact loop (5) and forming, with the second segment (15), a second elbow (13) with a concavity directed towards the contact loop (5).

12. A lens as claimed in claim 11, wherein the second elbow (13) defines an angle ($\gamma$2) between the second segment (15) and the third segment (16) of between 120° and 160°.

13. A lens as claimed in claim 7, wherein the second segment (15) has a length (l2) greater than that (l1) of the first segment (14).

14. A lens as claimed in claim 7, wherein the length (l2) of the second segment (15) lies between 1 mm and 3 mm.

15. A lens as claimed in claim 7, wherein the length (l1) of the first segment (14) lies between 0.5 mm and 1 mm.

16. A lens as claimed in claim 5, wherein each linking strand (10, 10') has a width (l) which is of the order of 0.5 mm.

17. A lens as claimed in claim 5, wherein the thickness (e) of each linking strand (10, 10') is the same as the thickness of the contact loop (5), and wherein this thickness (e) is less than an overall thickness (e') of the optic part (1).

18. A lens as claimed in claim 17, wherein the thickness (e) of the contact loops (5) and the linking strands (10, 10') lies between 0.2 mm and 0.4 mm.

19. A lens as claimed in claim 5, wherein the junction zone (17) of a linking strand (10, 10') with the periphery of the optic part (1) is disposed at least substantially in the extension of a radius (21) of the optic part (1) forming with the horizontal principal axis (8) an angle (θ1) of between 20° and 45°.

20. A lens as claimed in claim 5, wherein each linking strand (10, 10') is linked to a contact loop (5) in a junction zone (18) disposed on a radius (25) of the circle (Ca) passing through the apex (S) and the two end points (E, E'), this radius (25) forming with the horizontal principal axis (8) an angle (θ2) of between 45° and 75°.

21. A lens as claimed in claim 1, wherein each linking element (10, 10') is inscribed in an angular sector (11) of which the centre corresponds to that of the optic part (1) and is at least substantially a bisector of the two principal horizontal (8) and vertical (6) axes.

22. A lens as claimed in claim 21, wherein the said angular sector (11) extends over an angle (β) of between 20° and 40°.

23. A lens as claimed in claim 1, wherein each contact loop (5) extends between the end points (E, E') over an angular sector defined by the circle (Ca) passing through the apex (S) and the two end points (E, E'), with an angle (α) greater than or equal to 60° and less than 180°.

24. A lens as claimed in claim 1, wherein the contact loops (5) and the linking elements (10, 10') extend at least substantially over the principal plane (3), the lens having zero tilt.

25. A lens as claimed in claim 1, wherein each contact loop (5) is formed of a curved arc with a width which is at least substantially constant extending between the two free ends (7, 7').

26. A lens as claimed in claim 1, wherein the width (14) of each contact loop (5) is of the order of 0.5 mm.

27. A lens as claimed in claim 1, wherein the radius of curvature of the trace of the external surface (9) of each contact loop (5) in the principal plane (3) has a value at the apex (S) which is different from its value at the end points (E, E') and exhibits a monotonic variation between the apex (S) and each end point (E, E').

28. A lens as claimed in claim 1, wherein the trace of the external surface (9) of each contact loop (5) in the principal plane (3) is a portion of a conic curve.

29. A lens as claimed in claim 1, wherein the trace in the principal plane (3) of the external surface (9) of each contact loop (5) is a portion of a circle of diameter φa.

30. A lens as claimed in claim 1, wherein φa is greater than or equal to φm+0.2 mm and less than or equal to φm+0.7 mm.

31. A lens as claimed in claim 1, wherein φa lies between 8.5 mm and 11 mm.

32. A lens as claimed in claim 1 intended to be implanted in the capsular sac of an adult male, wherein φa is greater than or equal to 9.5 mm and less than or equal to 10.5 mm.

33. A lens as claimed in claim 1 intended to be implanted in the capsular sac of a child, wherein φa is greater than or equal to 8.5 mm and less than or equal to 9.5 mm.

34. A lens as claimed in claim 1, wherein D is greater than or equal to φa+1 mm and less than or equal to φa+2 mm.

35. A lens as claimed in claim 1, intended to be implanted in the capsular sac, wherein D lies between 11 mm and 12 mm.

* * * * *

UNITED STATES PATENT AND TRADEMARK OFFICE
CERTIFICATE OF CORRECTION

PATENT NO. : 6,409,762 B1
DATED : June 25, 2002
INVENTOR(S) : Joël Pynson et al.

It is certified that error appears in the above-identified patent and that said Letters Patent is hereby corrected as shown below:

<u>Title page,</u>
Item [86], amend to read as follows:

--     [86] PCT No.:   PCT/FR99/00589
        §371 (c) (1),
        (2), (4) Date:   Sep. 19, 2000 --.

Signed and Sealed this

Twenty-sixth Day of November, 2002

Attest:

JAMES E. ROGAN
*Attesting Officer*     *Director of the United States Patent and Trademark Office*